(12) United States Patent
Andree et al.

(10) Patent No.: US 6,548,449 B1
(45) Date of Patent: Apr. 15, 2003

(54) SUBSTITUTED PHENYLURACILS WITH HERBICIDAL EFFECT

(75) Inventors: Roland Andree, Langenfeld (DE); Markus Dollinger, Overland Park, KS (US); Mark Wilhelm Drewes, Langenfeld (DE); Ingo Wetcholowsky, Estancia Marambaia (BR); Randy Allen Myers, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,724
(22) PCT Filed: Jan. 16, 1999
(86) PCT No.: PCT/EP99/00237
§ 371 (c)(1), (2), (4) Date: Sep. 5, 2000
(87) PCT Pub. No.: WO99/38851
PCT Pub. Date: Aug. 5, 1999

(30) Foreign Application Priority Data

Jan. 29, 1998 (DE) .......................... 198 03 396

(51) Int. Cl.$^7$ ................ A01N 43/54; C07D 239/54
(52) U.S. Cl. .................. 504/243; 544/309; 544/310; 544/311; 544/312; 544/313; 544/314
(58) Field of Search ............... 504/243; 544/309, 544/310, 311, 312, 313, 314

(56) References Cited

U.S. PATENT DOCUMENTS 5,399,543 A * 3/1995 Theodoridis ............... 504/243

FOREIGN PATENT DOCUMENTS

| CA | 2083071 | 6/1993 |
|----|---------|--------|
| JP | 4-178373 | 6/1992 |
| WO | 95/17096 | 6/1995 |

* cited by examiner

*Primary Examiner*—John M. Ford
(74) *Attorney, Agent, or Firm*—Richard E. L. Henderson; Raymond J. Harmuth; Joseph C. Gil

(57) ABSTRACT

The invention relates to novel substituted phenyluraciles of the general formula (I)

in which m, n, Q and $R^{1-7}$ are each as defined in the description, and to processes for their preparation and to their use as herbicides.

11 Claims, No Drawings

SUBSTITUTED PHENYLURACILS WITH HERBICIDAL EFFECT

This is a 371 National Application of PCT/EP99/00237, filed Jan. 16, 1999.

The invention relates to novel substituted phenyluraciles, to processes for their preparation and to their use as herbicides.

A large number of substituted aryluraciles is already known from the (patent) literature (cf. U.S. Pat. No. 5,399,543, WO-A-95 17 096). However, these compounds have hitherto not attained any particular significance.

This invention, accordingly, provides novel substituted phenyluraciles of the general formula (I)

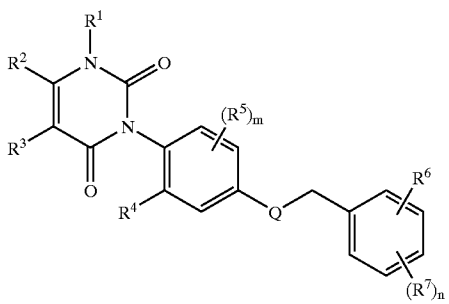

in which
m represents the numbers 0,1 or 2,
n represents the numbers 0, 1, 2 or 3,
Q represents O, S, SO, $SO_2$, NH or N(alkyl),
$R^1$ represents hydrogen, amino or optionally substituted alkyl,
$R^2$ represents carboxyl, cyano, carbamoyl, thiocarbamoyl, or represents in each case optionally substituted alkyl or alkoxycarbonyl,
$R^3$ represents hydrogen, halogen or optionally substituted alkyl,
$R^4$ represents hydrogen, cyano or halogen,
$R^5$ represents nitro, amino, hydroxyl, carboxyl, cyano, carbamoyl, thiocarbamoyl, sulpho, chlorosulphonyl, aminosulphonyl, halogen, or represents in each case optionally substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino or alkylsulphonylamino, and
$R^6$ represents nitro, amino or represents one of the groupings below —NH—$R^8$, —N($R^8$)$_2$, —NH—$SO_2$—$R^8$, —N($R^8$)(SO2—$R^8$), —N($SO_2$—$R^8$)$_2$, —NH—CO—$R^9$, —N($R^8$)(CO—$R^9$), —N(CO—$R^9$)$_2$, —N($SO_2$—$R^8$)(CO—$R^9$),
$R^7$ represents nitro, amino, hydroxyl, mercapto, carboxyl, cyano, carbamoyl, thiocarbamoyl, sulpho, chlorosulphonyl, aminosulphonyl, halogen, or represents in each case optionally substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino, alkylsulphonyl-amino or bis-alkylsulphonyl-amino,
$R^8$ represents in each case optionally substituted alkyl, alkenyl, cycloalkyl, aryl, arylalkyl or heterocyclyl, and
$R^9$ represents hydrogen or represents in each case optionally substituted alkyl, alkoxy, alkylamino, dialkylamino, alkenyl, alkinyl, cycloalkyl, cycloalkylalkyl, aryl, arylalkyl, heterocyclyl or heterocyclylalkyl, except for the prior-art compounds 1-[4-(4-nitro-phenylmethoxy-phenyl)]-3-methyl-4-trifluoromethyl-3,6-dihydro-2,6-dioxo-1(2H)-pyrimidine and 1-[2-fluoro-4-(4-nitro-phenylmethoxy-phenyl)]-3-methyl-4-trifluoromethyl-3,6-dihydro-2,6-dioxo-1(2H)-pyrimidine (cf. U.S. Pat. No. 5,399,543 and WO-A-95 17 096).

In the definitions, the hydrocarbon chains, such as alkyl—including in combination with heteroatoms, such as an alkoxy—are in each case straight-chain or branched.

The invention preferably provides substituted phenyluraciles of the formula (I) in which
m represents the numbers 0, 1 or 2,
n represents the numbers 0, 1, 2 or 3,
Q represents O, S, SO, $SO_2$, NH or N($C_1$–$C_4$-alkyl),
$R^1$ represents hydrogen, amino or optionally cyano-, halogen- or $C_1$–$C_4$-alkoxy-substituted alkyl having 1 to 6 carbon atoms,
$R^2$ represents carboxyl, cyano, carbamoyl, thiocarbamoyl, or represents in each case optionally cyano-, halogen- or $C_1$–$C_4$-alkoxy-substituted alkyl or alkoxycarbonyl having in each case up to 6 carbon atoms,
$R^3$ represents hydrogen, halogen or optionally cyano-, halogen- or $C_1$–$C_4$-alkoxy-substituted alkyl having 1 to 6 carbon atoms,
$R^4$ represents hydrogen, cyano or halogen,
$R^5$ represents nitro, amino, hydroxyl, carboxyl, cyano, carbamoyl, thiocarbamoyl, sulpho, chlorosulphonyl, aminosulphonyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino or alkylsulphonylamino having in each case up to 6 carbon atoms, and
$R^6$ represents nitro, amino or one of the groupings below —NH—$R^8$, —N($R^8$)$_2$, —NH—$SO_2$—$R^8$, —N($R^8$)(SO2—$R^8$), —N($SO_2$—$R^8$)$_2$, —NH—CO—$R^9$, —N($R^8$)(CO—$R^9$), —N(CO—$R^9$)$_2$, —N($SO_2$—$R^8$)(CO—$R^9$),
$R^7$ represents nitro, amino, hydroxyl, mercapto, carboxyl, cyano, carbamoyl, thiocarbamoyl, sulpho, chlorosulphonyl, aminosulphonyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino, alkylsulphonylamino or bis-alkylsulphonyl-amino having in each case up to 6 carbon atoms,
$R^8$ represents optionally halogen-substituted alkyl having 1 to 6 carbon atoms, represents optionally halogen-substituted alkenyl having 2 to 6 carbon atoms, represents optionally cyano-, halogen- or $C_1$–$C_4$-alkyl-substituted cycloalkyl having 3 to 6 carbon atoms, represents in each case optionally nitro-, cyano-, thiocarbamoyl-, halogen-, $C_1$–$C_4$-alkyl, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or $C_1$–$C_4$-alkoxycarbonyl-substituted aryl or arylalkyl having in each case 6 or 10 carbon atoms in the aryl group and optionally 1 to 4 carbon atoms in the alkyl moiety, or represents optionally cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl- or $C_1$–C4-halogenoalkylsulphonyl-substituted heterocyclyl from the series consisting of furyl, thienyl, oxazolyl, isoxazolyl, pyrazolyl, pyridyl, pyrimidyl, and $R^9$ represents hydrogen, represents in each case optionally cyano-, halogen- or $C_1$–$C_4$-alkoxy-substituted alkyl, alkoxy, alkylamino or dialkylamino having in each case 1 to 6 carbon atoms, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, represents in each case optionally nitro-, cyano-, thiocarbamoyl-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or $C_1$–$C_4$-alkoxycarbonyl-substituted aryl or arylalkyl having in each case 6 or 10 carbon atoms in the aryl group and optionally 1 to 4 carbon atoms in the alkyl moiety, or represents optionally cyano-, halogen-, C1-$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl- or $C_1$–$C_4$-halogenoalkylsulphonyl-substituted heterocyclyl from the series consisting of furyl, thienyl, oxazolyl, isoxazolyl, pyrazolyl, pyridyl, pyrimidyl, except for the prior-art compounds 1-[4-(4-nitrophenylmethoxy-phenyl)]-3-methyl-4-tri fluoromethyl-3,6-dihydro-2,6-dioxo-1(2H)-pyrimidine and 1-[2-fluoro-4-(4-nitro-phenylmethoxy-phenyl)]-3-methyl-4-trifluoromethyl-3,6-dihydro-2,6-dioxo-1(2H)-pyrimidine (cf. U.S. Pat. No. 5,399,543 and WO-A-95 17 096).

The invention relates in particular to compounds of the formula (I) in which m represents the numbers 0, 1 or 2, n represents the numbers 0, 1 or 2, Q represents O, S, SO, $SO_2$, NH or $N(CH_3)$, $R^1$ represents hydrogen, amino or represents in each case optionally cyano-, fluorine-, chlorine-, methoxy- or ethoxy-substituted methyl, ethyl, n- or i-propyl, n-, i-, s- or t-butyl, $R^2$ represents carboxyl, cyano, carbamoyl, thiocarbamoyl, or represents in each case optionally cyano-, fluorine-, chlorine-, methoxy- or ethoxy-substituted methyl, ethyl, n- or i-propyl, n-, i-, s- or t-butyl, methoxycarbonyl, ethoxycarbonyl, n- or i-propoxycarbonyl, $R^3$ represents hydrogen, fluorine, chlorine, bromine, or represents in each case optionally cyano-, fluorine-, chlorine-, methoxy- or ethoxy-substituted methyl, ethyl, n- or i-propyl, n-, i-, s- or t-butyl, $R^4$ represents hydrogen, cyano, fluorine or chlorine, $R^5$ represents nitro, amino, hydroxyl, carboxyl, cyano, carbamoyl, thiocarbamoyl, sulpho, chlorosulphonyl, aminosulphonyl, fluorine, chlorine, bromine, or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamillo, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, and $R^6$ represents nitro, amino or represents one of the groupings below —NH—$R^8$, —N($R^8$)$_2$, —NH—$SO_2$—$R^8$, —N($R^8$)(SO2—$R^8$), —N($SO_2$—$R^8$)$_2$, —NH—CO—$R^9$, —N($R^8$)(CO—$R^9$), —N(CO—$R^9$)$_2$, —N($SO_2$—$R^8$)(CO—$R^9$), $R^7$ represents nitro, amino, hydroxyl, mercapto, carboxyl, cyano, carbamoyl, thiocarbamoyl, sulpho, chlorosulphonyl, aminosulphonyl, fluorine, chlorine, bromine, or represents in each case optionally cyano-, fluorine-, chlorine-, methoxy- or ethoxy-substituted methyl, ethyl, n- or i-propyl, n-, i-, s- or .t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylamino-carbonyl, n- or i-propylaminocarbonyl, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, bis-(methylsulphonyl)-amino or bis-(ethylsulphonyl)-amino, $R^8$ represents in each case optionally fluorine and/or chlorine-substituted methyl, ethyl, n- or i-propyl, n-, i-, s- or t-butyl, represents in each case optionally fluorine- and/or chlorine-substituted ethenyl, propenyl or butenyl, represents in each case optionally cyano-, fluorine-, chlorine-, methyl- or ethyl-substituted cyclopropyl, cyclobutyl, cyclopentyl or cyclohexyl, represents in each case optionally nitro-, cyano-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, methoxycarbonyl- or ethoxy-carbonyl-substituted phenyl or benzyl, or represents optionally cyano-, fluorine-, chlorine-, bromine-, methyl-, ethyl-, n- or i-propyl-, n-, i-, s- or t-butyl, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, trifluoromethylthio-, methylsulphinyl-, ethylsulphinyl-, trifluoromethylsulphonyl-, methylsulphonyl-, ethylsulphonyl-, or trifluoromethylsulphonyl-substituted heterocyclyl from the series consisting of furyl, thienyl, oxazolyl, isoxazolyl, pyrazolyl, pyridyl, pyrimidyl, and $R^9$ represents hydrogen, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methyl-amino, ethylamino, n- or i-propylamino, n-, i-, s- or t-butylamino or dimethylamino, represents in each case optionally cyano-, fluorine- or chlorine-substituted ethenyl, propenyl, butenyl, ethenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoro-methylsulphinyl-, methylsulphonyl-, ethylsulphonyl-, trifluoromethylsulphonyl-, methoxycarbonyl-, ethoxycarbonyl-, n- or i-propoxycarbonyl-substituted phenyl or benzyl, or represents optionally cyano-, fluorine-, chlorine-, bromine-, methyl-, ethyl-, n- or 1-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted heterocyclyl from the series consisting of furyl, thienyl, oxazolyl, isoxazolyl, pyrazolyl, pyridyl, pyrimidyl, except for the prior-art compounds 1-[4-(4-nitro-phenylmethoxy-phenyl)]-3-methyl-4-trifluoromethyl-3,6-dihydro-2,6-dioxo-1(2H)-pyrimidine and 1-[2-fluoro-4-(4-nitro-phenylmethoxy-phenyl)]-3-methyl-4-trifluoromethyl-3,6-dihydro-2,6-dioxo-1(2H)-pyrimidine (cf. U.S. Pat. No. 5,399,543 and WO-A-95 17 096).

Very particular preference is given to compounds of the formula (I) in which m represents the number 0, n represents the numbers 0 or 1, Q represents O, $R^1$ represents hydrogen, amino or methyl, $R^2$ represents trifluoromethyl, $R^3$ represents hydrogen, $R^4$ represents fluorine or chlorine, $R^6$ represents nitro, amino or represents one of the groupings below —NH—SO$_2$—$R^8$ or —N(SO$_2$—$R^8$)(CO—$R^9$), $R^7$ represents nitro, cyano, fluorine, chlorine, bromine or represents optionally fluorine-substituted methyl or methoxy, in particular in the 4-position, $R^8$ represents methyl or ethyl, and $R^9$ represents methyl, ethyl, n- or i-propyl, n-, i-, s- or t-butyl or phenyl.

The abovementioned general or preferred radical definitions apply both to the end products of the formula (I) and, correspondingly, to the starting materials or intermediates required in each case for the preparation. These radical definitions can be combined with one another at will, i.e. including combinations between the given preferred ranges.

The novel phenyluraciles of the general formula (I) have strong and selective herbicidal activity.

The novel substituted phenyluraciles of the general formula (I) are obtained when (a) phenyluraciles of the general formula (II)

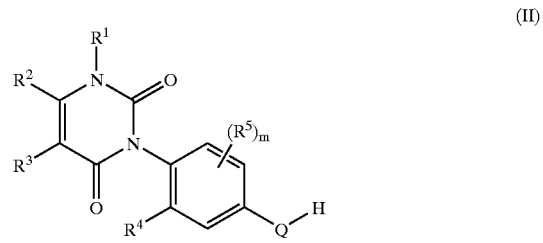

in which
m, Q, $R^1$, $R^2$, $R^3$, $R^4$ and $R^5$ are each as defined above,
are reacted with substituted benzyl halides of the general formula (III)

in which
n, $R^6$ and $R^7$ are each as defined above and
$X^1$ represents halogen,
if appropriate in the presence of a reaction auxiliary and
if appropriate in the presence of a diluent,
or when (b) substituted phenyluraciles of the general formula (Ia)

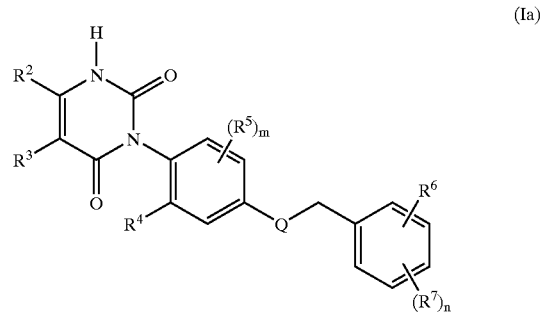

in which
m, n, Q, $R^2$, $R^3$, $R^4$, $R^5$, $R^6$ and $R^7$ are each as defined above,
are reacted with 1-aminooxy-2,4-dinitro-benzene or with alkylating agents of the general formula (IV)

$$X^2—A^1 \qquad (IV)$$

in which

A¹ represents optionally substituted alkyl and

X² represents halogen or the grouping —O—SO₂—O—A¹, if appropriate in the presence of a reaction auxiliary and if appropriate in the presence of a diluent, and, if appropriate, electrophilic or nucleophilic and/or oxidation or reduction reactions within the scope of the definition of the substituents are carried out subsequently in a customary manner.

Using, for example, 1-(2-chloro-4-mercapto-phenyl)-4-trifluoromethyl-3,6-dihydro-2,6-dioxo-1(2H)-pyrimidine and 4-fluoro-3-nitro-benzyl chloride as starting materials, the course of the reaction in the process (a) according to the invention can be illustrated by the following formula scheme:

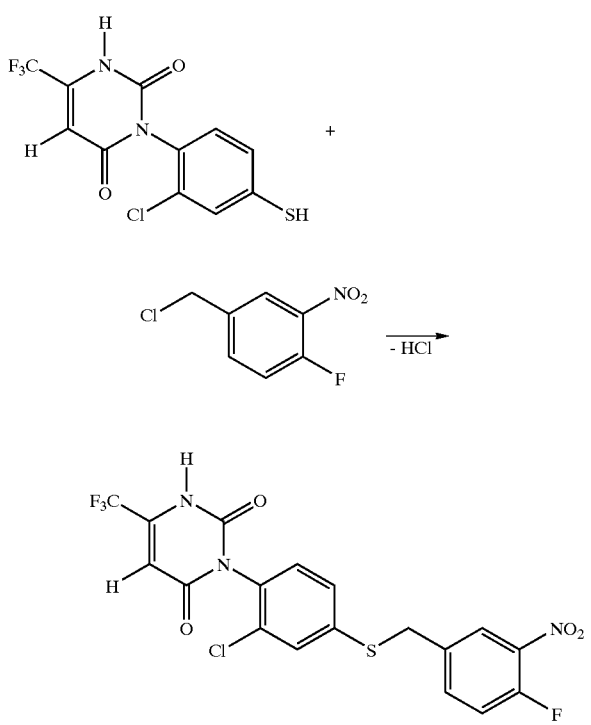

Using, for example, 1-[²-fluoro-4-(4-bromo-3-nitro-benzyloxy)-phenyl]-4-trifluoromethyl-3,6-dihydro-2,6-dioxo-1(2H)-pyrimidine and ethyl bromide as starting materials, the course of the reaction in the process (b) according to the invention can be illustrated by the following formula scheme:

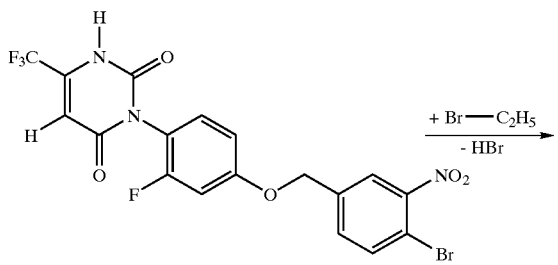

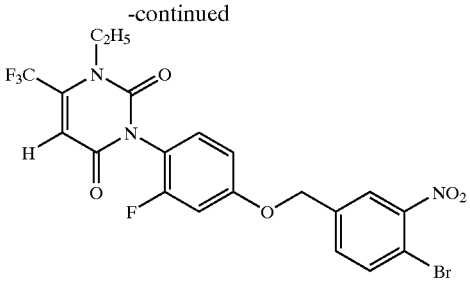

The formula (II) provides a general definition of the phenyluraciles to be used as starting materials in the process (a) according to the invention for preparing compounds of the formula (I). In the formula (II), m, Q, $R^1$, $R^2$, $R^3$, $R^4$ and $R^5$ each preferably or in particular have those meanings which have already been mentioned above, in connection with the description of the compounds of the formula (I) according to the invention, as being preferred or as being particularly preferred for m, Q, $R^1$, $R^2$, $R^3$, $R^4$ and $R^5$.

The starting materials of the general formula (II) are known and/or can be prepared by processes known per se (cf. EP-A-545 206, JP-A-04 178 373, Preparation Examples).

The formula (III) provides a general definition of the substituted benzyl halides further to be used as starting materials in the process of (a) according to the invention. In the formula (III), n, $R^6$ and $R^7$ each preferably or in particular have those meanings which have already been mentioned above, in connection with the description of the compounds of the formula (I) according to the invention, as being preferred or as being particularly preferred for n, $R^6$ and $R^7$; $X^1$ preferably represents fluorine, chlorine, bromine or iodine, in particular chlorine or bromine.

The starting materials of the general formula (III) are known organic chemicals for synthesis.

The formula (Ia) provides a general definition of the substituted phenyluraciles to be used as starting materials in the process (b) according to the invention for preparing compounds of the formula (I). In the formula (Ia), m, n, Q, $R^2$, $R^3$, $R^4$, $R^5$, $R^6$ and $R^7$ each preferably or in particular have those meanings which have already been mentioned above, in connection with the description of the compounds of the formula (I) according to the invention, as being preferred or as being particularly preferred for m, n, Q, $R^2$, $R^3$, $R^4$, $R^5$, $R^6$ and $R^7$.

As novel substances, the starting materials of the general formula (Ia) for process (b) also form part of the subject-matter of the present application; they can be prepared by the process (a) according to the invention.

The formula (IV) provides a general definition of the alkylating agents further to be used as starting materials in the process (b) according to the invention. In the formula (IV), $A^1$ preferably represents optionally cyano-, halogen- or $C_1$–$C_4$-alkoxy-substituted alkyl having 1 to 4 carbon atoms and $X^2$ preferably represents chlorine, bromine, iodine, methylsulphonyloxy or ethylsulphonyloxy; in particular, $A^1$ represents in each case optionally cyano-, fluorine-, chlorine-, methoxy- or ethoxy-substituted methyl, ethyl, n- or i-propyl and $X^2$ represents chlorine, bromine, iodine, methylsulphonyloxy or ethylsulphonyloxy.

The starting materials of the formula (IV) are known organic chemicals for synthesis.

The processes according to the invention for preparing the compounds of the general formula (I) are preferably carried out using diluents. Suitable diluents for carrying out the processes (a) and (b) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethyleneglycol monoethyl ether, diethylene glycol monomethyl ether, diethylene glycol monoethyl ether, mixtures thereof with water or pure water.

Suitable reaction auxiliaries for the processes (a) and (b) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8 diazabicyclo[5,4,0]-undec-7-ene (DBU).

Other suitable reaction auxiliaries for the processes (a) and (b) according to the invention are phase-transfer catalysts. Examples of such catalysts which may be mentioned are: tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

When carrying out the processes (a) and (b) according to the invention, the reaction temperatures can be carried within a relatively wide range. In general, the processes are carried out at temperatures between 0° C. and 150° C., preferably between 10° C. and 120° C.

The processes according to the invention are generally carried out under atmospheric pressure. However, it is also possible to carry out the processes according to the invention under elevated or reduced pressure—generally between 0.1 bar and 10 bar.

For carrying out the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for several hours. Work-up is carried out by customary methods (cf. the preparation examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial sites and rail tracks and on paths and squares with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention are particularly suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formnulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethyl-formamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides, finished formulations or tank mixes being possible.

Possible Components for the Mixtures are Known Herbicides, for Example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinmethylin, cinosulfuron, clethodim, clodinafop(-propargyl), clomazone, clomeprop, clopyralid, clopyrasulfuron(-methyl), cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), flamprop(-isopropyl), flamprop(-isopropyl-L), flamprop(-methyl), flazasulfuron, fluazifop(-P-butyl), flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate-(-isopropylammonium), halosafen, haloxyfop(-ethoxyethyl), haloxyfop(-p-methyl), hexazinone, imazamethabenz-(-methyl), imazamethapyr, imazamox, imazapyr, imazaquin, imazethapyr, imazosulfuron, ioxynil, isopropalin, isoproturon, isouron, isoxaben, isoxaflutole, isoxapyrifop, lactofen, lenacil, linuron, MCPA, MCPP, mefenacet, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quimmerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifen-sulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

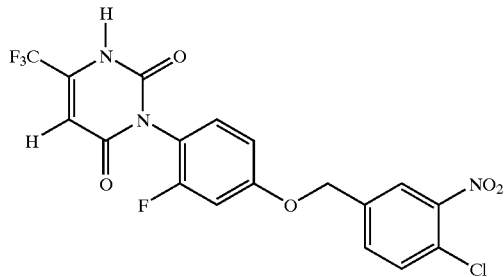

(Process (a))

A mixture of 16.5 g (57 mmol) of 1-(2-fluoro-4-hydroxy-phenyl)-4-trifluoromethyl-3,6-dihydro-2,6-dioxo-1(2H)-pyrimidine, 12.35 g (60 mmol) of 4-chloro-3-nitro-benzyl chloride, 16.5 g of potassium carbonate, 1.5 g of benzyl-triethylammonium chloride and 300 ml of acetonitrile is heated under reflux for 4 hours and then concentrated under water pump vacuum. The residue is taken up in 1N hydrochloric acid and extracted with ethyl acetate. The organic phase is washed with 1N hydrochloric acid, dried with sodium sulphate and filtered. The filtrate is concentrated under water pump vacuum, the residue is crystallized by digestion with ethyl acetate/diethyl ether/petroleum ether and the crystalline product is isolated by filtration with suction.

This gives 9.3 g (90% of theory) of 1-[2-fluoro-4-(4-chloro-3-nitro-benzyloxy)-phenyl]-4-trifluoromethyl-3,6-dihydro-2,6-dioxo-1(2H)-pyrimidine of melting point 165° C.

Example 2

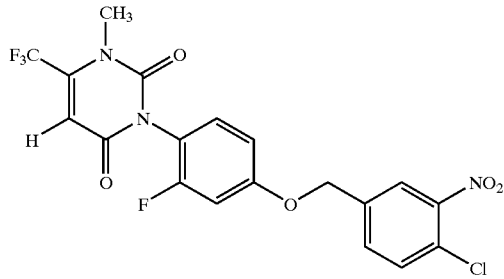

(Process (b))

A mixture of 4.0 g (8.7 mmol) of 1-[2-fluoro-4-(4-chloro-3-nitro-benzyloxy)-phenyl]-4-trifluoromethyl-3,6-dihydro-2,6-dioxo-1(2H)-pyrimidine, 1.25 g (10 mmol) of dimethyl sulphate, 1.4 g of potassium carbonate and 30 ml of acetone is heated under reflux for 30 minutes and then concentrated under water pump vacuum. The residue is stirred with 1N hydrochloric acid and diethyl ether and the resulting crystalline product is isolated by filtration with suction.

This gives 3.5 g (90% of theory) of 1-[2-fluoro-4-(4-chloro-3-nitro-benzyloxy)-phenyl]-3-methyl-4-trifluoromethyl-3,6-dihydro-2,6-dioxo-1 (2H)-pyrimidine of melting point 133° C.

Example 3

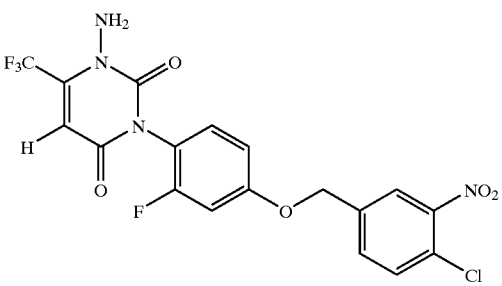

(Process (b))

A mixture of 4.0 g (8.7 mmol) of 1-[2-fluoro-4-(4-chloro-3-nitro-benzyloxy)-phenyl]-4-trifluoromethyl-3,6-dihydro-2,6-dioxo-1(2H)-pyrimidine, 2.7 g (13.6 mmol) of 1-aminooxy-2,4-dinitro-benzene, 1.2 g of sodium bicarbonate and 10 ml of N,N-dimethyl-formamide is stirred at room temperature (approximately 20° C.) for 5 days. The mixture is then diluted with 0.1% strength aqueous sodium hydroxide solution and extracted with diethyl ether. The organic phase is washed with 0.1% strength aqueous sodium hydroxide solution, with water and with 0.1% strength aqueous sodium dihydrogen phosphate solution, dried with sodium sulphate and filtered. The filtrate is concentrated under water pump vacuum, the residue is digested with diethyl ether and the resulting crystalline product is isolated by filtration with suction.

This gives 3.0 g (73% of theory) of 3-amino-1-[2-fluoro-4-(4-chloro-3-nitro-benzyl-oxy)-phenyl]-4-trifluoromethyl-3,6-dihydro-2,6-dioxo-1(2H)-pyrimidine of melting point 185° C.

Example 4

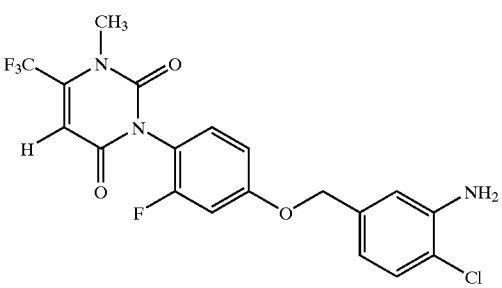

(Subsequent Reaction)

A mixture of 3.0 g (6.3 mmol) of 1-[2-fluoro-4-(4-chloro-3-nitro-benzyloxy)-phenyl]-3-methyl-4-trifluoromethyl-3,6-dihydro-2,6-dioxo-1(2H)-pyrimidine, 40 ml of acetic acid and 10 ml of water is, at 50° C. and with stirring, admixed a little at a time with 1.8 g or iron (powder), then stirred at room temperature (approximately 20° C.) for 90 minutes and subsequently concentrated under water pump vacuum. The residue is taken up in water and extracted with ethyl acetate. The organic phase is washed with water, 0.1% strength aqueous sodium hydroxide solution and 1% strength hydrochloric acid, dried with sodium sulphate and filtered. The filtrate is concentrated under water pump vacuum, the residue is digested with diethyl ether/petroleum ether and the resulting crystalline product is isolated by filtration with suction.

This gives 2.2 g (78.5% of theory) of 1-[2-fluoro-4-(3-amino-4-chloro-benzyloxy)-phenyl]-3-methyl-4-trifluoromethyl-3,6-dihydro-2,6-dioxo-1(2H)-pyrimidine of melting point 148° C.

Example 5

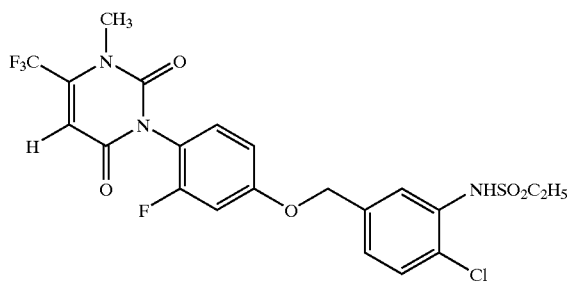

(Subsequent Reaction)

At 50° C., a mixture of 1.8 g (4.05 mmol) of 1-[2-fluoro-4-(3-amino-4-chloro-benzyloxy)-phenyl]-3-methyl-4-trifluoromethyl-3,6-dihydro-2,6-dioxo-1(2H)-pyrimidine, 0.35 g of pyridine, a spatula tip of 4-dimethylamino-pyridine and 10 ml of acetonitrile is admixed with 0.65 g (5 mmol) of ethanesulphonyl chloride and the reaction mixture is heated under reflux for 2 hours. After addition of a further 0.5 g of pyridine and a further 0.65 g of ethanesulphonyl chloride, [lacuna] heated under reflux for a further 2 hours and subsequently concentrated under water pump vacuum. The residue is taken up in 1% strength aqueous sodium dihydrogen-phosphate solution and extracted with ethyl acetate. The organic phase is washed with water, dried with sodium sulphate and filtered. The residue is purified by column chromatography (silica gel, hexane/ethyl acetate, Vol.: 3:1).

This gives 0.60 g (28% of theory) of 1-[2-fluoro-4-(4-chloro-3-ethylsulphonylamino-benzyloxy)-phenyl]-3-methyl-4-trifluoromethyl-3,6-dihydro-2,6-dioxo-1(2H)-pyrimidine of melting point 151 ° C.

Analogously to the Preparation Examples 1 to 5 and in accordance with the general description of the preparation processes according to the invention, it is also possible to prepare, for example, compounds of the formula (I) listed in Table 1 below.

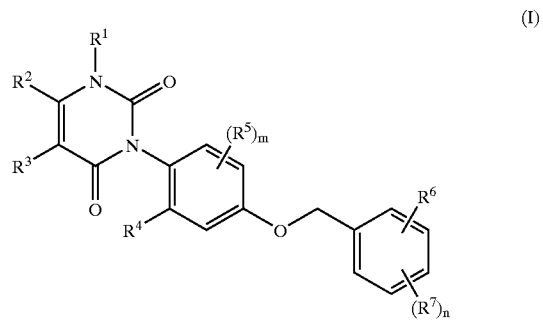

(I)

TABLE 1

Examples of the compounds of the formula (I)

| Ex. No. | $R^1$ | $R^2$ | $R^3$ | $R^4$ | (Position) $(R^5)_m$ | (Position)$R^6$ | (Position) $(R^7)_n$ | Melting point (° C.) |
|---|---|---|---|---|---|---|---|---|
| 7 | $NH_2$ | $CF_3$ | H | F | — | (3-) $NH_2$ | (4-) Cl | 206 |
| 8 | $NH_2$ | $CF_3$ | H | F | — | (3-) $NHSO_2C_2H_5$ | (4-) Cl | 95 |
| 9 | $CH_3$ | $CF_3$ | H | F | — | (3-) $NHSO_2CH_3$ | (4-) Cl | |
| 10 | $NH_2$ | $CF_3$ | H | F | — | (3-) $NHSO_2CH_3$ | (4-) Cl | |
| 11 | $CH_3$ | $CF_3$ | H | F | — | (3-) N(COCH$_3$)(SO$_2$C$_2$H$_5$) | (4-) Cl | |
| 12 | $CH_3$ | $CF_3$ | H | F | — | (3-) N(COC(CH$_3$)$_3$)(SO$_2$C$_2$H$_5$) | (4-) Cl | |
| 13 | $CH_3$ | $CF_3$ | H | F | — | (3-) N(COC$_6$H$_5$)(SO$_2$C$_2$H$_5$) | (4-) Cl | |
| 14 | $CH_3$ | $CF_3$ | 14 | F | — | (3-) $NO_2$ | (4-) CN | |
| 15 | $CH_3$ | $CF_3$ | H | F | — | (3-) $NO_2$ | (4-) $NO_2$ | |
| 16 | $CH_3$ | $CF_3$ | H | F | — | (3-) $NO_2$ | (4-) F | |
| 17 | $CH_3$ | $CF_3$ | H | F | — | (3-) $NO_2$ | (4-) Br | |
| 18 | $CH_3$ | $CF_3$ | H | F | — | (3-) $NH_2$ | (4-) F | |
| 19 | $CH_3$ | $CF_3$ | H | F | — | (3-) $NH_2$ | (4-) Br | |
| 20 | $CH_3$ | $CF_3$ | H | F | — | (3-) $NO_2$ | (4-) Cl | |
| 21 | $CH_3$ | $CF_3$ | H | H | — | (3-) $NO_2$ | — | 154 |
| 22 | $CH_3$ | $CF_3$ | H | F | — | (3-) $NH_2$ | (4-) CN | |
| 23 | $CH_3$ | $CF_3$ | H | F | — | (3-) $NHSO_2CH_3$ | (4-) CN | |
| 24 | $CH_3$ | $CF_3$ | H | F | — | (3-) $NHSO_2C_2H_5$ | (4-) CN | |
| 25 | $CH_3$ | $CF_3$ | H | F | — | (3-) $NO_2$ | (4-) $CF_3$ | |
| 26 | $CH_3$ | $CF_3$ | H | F | — | (3-) $NH_2$ | (4-) $CF_3$ | |

TABLE 1-continued

Examples of the compounds of the formula (I)

| Ex. No. | $R^1$ | $R^2$ | $R^3$ | $R^4$ | (Position) $(R^5)_m$ | (Position)$R^6$ | (Position) $(R^7)_n$ | Melting point (° C.) |
|---|---|---|---|---|---|---|---|---|
| 27 | $CH_3$ | $CF_3$ | H | F | — | (3-) $NHSO_2CH_3$ | (4-) $CF_3$ | |
| 28 | $CH_3$ | $CF_3$ | H | F | — | (3-) $NHSO_2C_2H_5$ | (4-) $CF_3$ | |
| 29 | $CH_3$ | $CF_3$ | H | F | — | (5-) $NHSO2C_2H_5$ | (2-) F (4-) Cl | |
| 30 | $CH_3$ | $CF_3$ | H | H | — | (5-) $NHSO_2C_2H_5$ | (2-) F (4-) Cl | |
| 31 | $CH_3$ | $CF_3$ | H | F | — | (3-) $NO_2$ | (4-) $CH_3$ | |
| 32 | $CH_3$ | $CF_3$ | H | F | — | (3-) $NH_2$ | (4-) $CH_3$ | |
| 33 | $CH_3$ | $CF_3$ | H | F | — | (3-) $NO_2$ | (4-) $OCH_3$ | |
| 34 | $CH_3$ | $CF_3$ | H | F | — | (3-) $NH_2$ | (4-) $OCH_3$ | |
| 35 | $CH_3$ | $CF_3$ | H | F | — | (3-) $NO_2$ | (4-) $OCF_3$ | |
| 36 | $CH_3$ | $CF_3$ | H | F | — | (3-) $NH_2$ | (4-) $OCF_3$ | |
| 37 | $CH_3$ | $CF_3$ | H | F | — | (3-) $NH_2$ | — | (amorphous) |
| 38 | $CH_3$ | $CF_3$ | H | F | — | (4-) $NH_2$ | — | |
| 39 | $CH_3$ | $CF_3$ | H | F | — | (2-) $NH_2$ | — | |
| 40 | $CH_3$ | $CF_3$ | H | F | — | (3-) $NHSO_2CH_3$ | — | |
| 41 | $CH_3$ | $CF_3$ | H | F | — | (2-) $NHSO_2CH_3$ | — | |
| 42 | $CH_3$ | $CF_3$ | H | F | — | (2-) $NH_2$ | (4-) Cl | |
| 43 | $CH_3$ | $CF_3$ | H | F | — | (2-) $NHSO_2CH_3$ | (4-) Cl | |
| 44 | $CH_3$ | $CF_3$ | H | Cl | — | (3-) $NO_2$ | (4-) Cl | |
| 45 | $CH_3$ | $CF_3$ | H | Cl | — | (3-) $NH_2$ | (4-) Cl | |
| 46 | $CH_3$ | $CF_3$ | H | Cl | — | (3-) $NHSO_2CH_3$ | (4-) Cl | |
| 47 | $CH_3$ | $CF_3$ | H | Cl | — | (3-) $NO_2$ | — | |
| 48 | $CH_3$ | $CF_3$ | H | Cl | — | (3-) $NH_2$ | — | |
| 49 | $CH_3$ | $CF_3$ | H | Cl | — | (3-) $NHSO_2CH_3$ | — | |
| 50 | H | $CF_3$ | H | H | — | (2-) $NO_2$ | — | 251 |
| 51 | H | $CF_3$ | H | H | — | (3-) $NO_2$ | — | (amorphous) |
| 52 | H | $CF_3$ | H | H | — | (4-) $NO_2$ | — | 207 |
| 53 | H | $CF_3$ | F | H | — | (3-) $NO_2$ | (4-) $CH_3$ | 241 |
| 54 | H | $CF_3$ | H | H | — | (2-) $NO_2$ | (5-) $CH_3$ | 234 |
| 55 | H | $CF_3$ | H | H | — | (3-) $NO_2$ | (4-) Cl | 162 |
| 56 | $CH_3$ | $CF_3$ | H | H | — | (2-) $NO_2$ | — | 207 |
| 57 | $CH_3$ | $CF_3$ | H | H | — | (2-) $NO_2$ | (5-) $CH_3$ | 215 |
| 58 | $CH_3$ | $CF_3$ | H | H | — | (3-) $NO_2$ | (4-) Cl | 100 |
| 59 | $CH_3$ | $CF_3$ | H | H | — | (3-) $NO_2$ | (4-) $CH_3$ | 223 |
| 60 | $CH_3$ | $CF_3$ | H | H | — | (2-) $NH_2$ | — | 167 |
| 61 | $CH_3$ | $CF_3$ | H | H | — | (2-) $NH_2$ | (5-) $CH_3$ | 177 |
| 62 | $CH_3$ | $CF_3$ | H | H | — | (3-) $NH_2$ | (4-) $CH_3$ | 183 |
| 63 | $CH_3$ | $CF_3$ | H | H | — | (2-) $NHSO_2C_2H_5$ | (5-) $CH_3$ | (amorphous) |
| 64 | $CH_3$ | $CF_3$ | H | H | — | (3-) $NHSO_2C_2H_5$ | (4-) $CH_3$ | (amorphous) |
| 65 | $CH_3$ | $CF_3$ | H | H | — | (3-) $NH_2$ | (4-) Cl | (amorphous) |
| 66 | $CH_3$ | $CF_3$ | H | H | — | (3-) $NH_2$ | — | 167 |
| 67 | $CH_3$ | $CF_3$ | H | H | — | (3-) $NHSO_2C_2H_5$ | — | 153 |
| 68 | H | $CF_3$ | H | F | — | (3-) $NO_2$ | — | 183 |
| 69 | $CH_3$ | $CF_3$ | H | F | — | (3-) $NO_2$ | — | 138 |
| 70 | $CH_3$ | $CF_3$ | H | F | — | (3-) $NHSO_2C_2H_5$ | — | (amorphous) |

Starting Materials of the Formula (II)

Example (II-1)

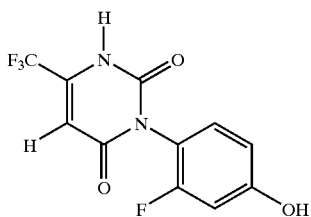

-continued

Step 1

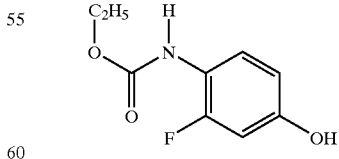

At 0° C., 9.1 g (84 mmol) of ethyl chloroformate are added dropwise with stirring to a mixture of 9.8 g (77 mmol) of 4-amino-3-fluoro-phenol, 2.3 g of magnesium oxide, 150 ml of ethyl acetate and 15 ml of water, and the reaction mixture is stirred at 0° C. for 60 minutes. The mixture is then diluted with 1% strength aqueous sodium dihydrogen phosphate solution to about twice its volume and the organic phase is separated off, washed with water, dried with sodium sulphate and filtered. The filtrate is concentrated under water pump vacuum, the residue is digested with diethyl ether/petroleum ether and the resulting crystalline product is isolated by filtration with suction.

This gives 14.2 g (93% of theory) of O-ethyl N-(2-fluoro-4-hydroxy-phenyl)-urethane of melting point 111° C.

Step 2

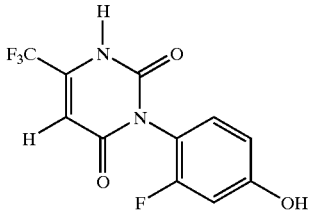

15.6 g (70 mmol) of ethyl 3-amino-4,4,4-trifluoro-crotonate are initially charged in 50 ml of N-methyl-pyrrolidone and, at room temperature (approximately 20° C.) admixed with 2.5 g of sodium hydride. The mixture is stirred at room temperature for 30 minutes and subsequently admixed with 14.0 g (70 mmol) of O-ethyl N-(2-fluoro-4-hydroxy-phenyl)-urethane. The reaction mixture is stirred at 140° C. for 45 minutes and then, after slight cooling, poured into about the same amount of ice-water. After shaking with ethyl acetate, the aqueous phase is separated off, acidified with 2N hydrochloric acid and extracted with ethyl acetate. The organic phase is dried with sodium sulphate and filtered. The filtrate is concentrated under water pump vacuum, the residue is digested with diethyl ether and the resulting crystalline product is isolated by filtration with suction.

This gives 17.15 g (84% of theory) of 1-(2-fluoro-4-hydroxy-phenyl)-4-trifluoromethyl-3,6-dihydro-2,6-dioxo-1(2H)-pyrimidine of melting point 239° C.

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compounds such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Example 5 and 7 exhibit very strong activity against weeds, whilst being tolerated well by crop plants, such as, for example, barley and cotton.

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifiers is added and the concentrate is diluted with water to the desired concentration.

Test plants of a height of 5–15 cm are sprayed with the preparation of active compound such that the particular amounts of active compound are employed per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Example 2, 3, 4, 5, 6 and 7 exhibit very strong activity against weeds, whilst some of them are tolerated well by crop plants, such as, for example, wheat.

What is claimed is:

1. A phenyluracil of the formula (I)

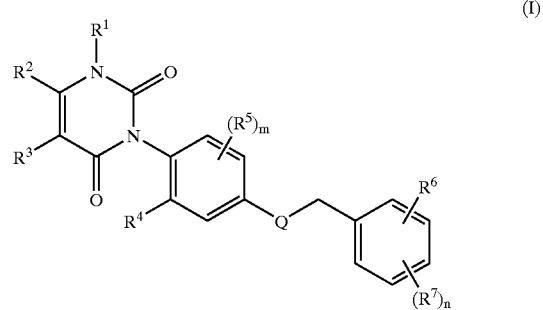

in which m represents the numbers 0, 1 or 2, n represents the numbers 0, 1, 2 or 3, Q represents O, S, SO, $SO_2$, NH or N($C_1$–$C_4$-alkyl), $R^1$ represents hydrogen, amino or optionally cyano-, halogen- or $C_1$–$C_4$-alkoxy-substituted alkyl having 1 to 6 carbon atoms, $R^2$ represents carboxyl, cyano, carbamoyl, thiocarbamoyl, or represents in each case optionally cyano-, halogen- or $C_1$–$C_4$-alkoxy-substituted alkyl or alkoxy-carbonyl having in each case up to 6 carbon atoms, $R^3$ represents hydrogen, halogen or optionally cyano-, halogen- or $C_1$–$C_4$-alkoxy-substituted alkyl having 1 to 6 carbon atoms, $R^4$ represents hydrogen, cyano or halogen, $R^5$ represents nitro, amino, hydroxyl, carboxyl, cyano, carbamoyl, thiocarbamoyl, sulpho, chlorosulphonyl, aminosulphonyl, halogen, or represents in each case optionally cyano-, halogen- or $C_1$–$C_4$-alkoxy-substituted alkyl, alkoxy, alkyl-thio, alkylsulphinyl, alkylsulphonyl, alkylamino, alkylcarbonyl, alkoxycarbonyl, alkylaminocarbonyl, alkylcarbonylamino, alkoxycarbonylamino or alkyl-sulphonylamino having in each case up to 6 carbon atoms, and R$^6$ represents amino or one of the groupings below —NH—R$^8$, —N(R$^8$)$_2$, —NH—SO$_2$—R$^8$, —N(R$^8$)(SO$_2$—R$^8$), —N(SO$_2$—R$^8$)$_2$, —NH—CO—R$^9$, —N(R$^8$)(CO—R$^9$), —N(CO—R$^9$)$_2$, —N(SO$_2$—R$^8$)(CO—R$^9$), R$^7$ represents nitro, amino, hydroxyl, mercapto, carboxyl, cyano, carbamoyl, thio-carbamoyl, sulpho, chlorosulphonyl, aminosulphonyl, halogen, or represents in each case optionally cyano-, halogen- or C$_1$–C$_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonyl-amino, alkylsulphonylamino or bis-alkylsulphonyl-amino having in each case up to 6 carbon atoms, R$^8$ represents optionally halogen-substituted alkyl having 1 to 6 carbon atoms, represents optionally halogen-substituted alkenyl having 2 to 6 carbon atoms, represents optionally cyano-, halogen- or C$_1$–C$_4$-alkyl-substituted cycloalkyl having 3 to 6 carbon atoms, represents in each case optionally nitro-, cyano-, thiocarbamoyl-, halogen-, C$_1$–C$_4$-alkyl, C$_1$–C$_4$-halogenoalkyl-, C$_1$–C$_4$-alkoxy-, C$_1$–C$_4$-halogenoalkoxy-, C$_1$–C$_4$-alkylthio-, C$_1$–C$_4$-halogenoalkylthio-, C$_1$–C$_4$-alkylsulphinyl-, C$_1$–C$_4$-halogenoalkylsulphinyl-, C$_1$–C$_4$-alkylsulphonyl-, C$_1$–C$_4$-halogenoalkylsulphonyl- or C$_1$–C$_4$-alkoxycarbonyl-substituted aryl or arylalkyl having in each case 6 or 10 carbon atoms in the aryl group and optionally 1 to 4 carbon atoms in the alkyl moiety, or represents optionally cyano-, halogen-, C$_1$–C$_4$-alkyl-, C$_1$–C$_4$-halogenoalkyl-, C$_1$–C$_4$-alkoxy-, C$_1$–C$_4$-halogenoalkoxy-, C$_1$–C$_4$-alkylthio-, C$_1$–C$_4$-halogenoalkylthio-, C$_1$–C$_4$-alkylsulphinyl-, C$_1$–C$_4$-halogenoalkylsulphinyl-, C$_1$–C$_4$-alkylsulphonyl- or C$_1$–C$_4$-halogenoalkyl-sulphonyl-substituted heterocyclyl selected from the group consisting of furyl, thienyl, oxazolyl, isoxazolyl, pyrazolyl, pyridyl and pyrimidyl, and R$^9$ represents hydrogen, represents in each case optionally cyano-, halogen- or C$_1$–C$_4$-alkoxy-substituted alkyl, alkoxy, alkylamino or dialkylamino having in each case 1 to 6 carbon atoms, represents in each case optionally cyano- or halogen-substituted alkenyl or alkinyl having in each case 2 to 6 carbon atoms, represents in each case optionally cyano-, halogen- or C$_1$–C$_4$-alkyl-substituted cycloalkyl or cycloalkylalkyl having in each case 3 to 6 carbon atoms in the cycloalkyl group and optionally 1 to 4 carbon atoms in the alkyl moiety, represents in each case optionally nitro-, cyano-, thiocarbamoyl-, halogen-, C$_1$–C$_4$-alkyl-, C$_1$–C$_4$-halogenoalkyl-, C$_1$–C$_4$-alkoxy-, C$_1$–C$_4$-halogenoalkoxy-, C$_1$–C$_4$-alkylthio-, C$_1$–C$_4$-halogenoalkylthio-, C$_1$–C$_4$-alkylsulphinyl-, C$_1$–C$_4$-halogenoalkylsulphinyl-, C$_1$–C$_4$-alkylsulphonyl-, C$_1$–C$_4$-halogenoalkylsulphonyl- or C$_1$–C$_4$-alkoxycarbonyl-substituted aryl or arylalkyl having in each case 6 or 10 carbon atoms in the aryl group and optionally 1 to 4 carbon atoms in the alkyl moiety, or represents optionally cyano-, halogen-, C$_1$–C$_4$-alkyl-, C$_1$–C$_4$-halogenoalkyl-, C$_1$–C$_4$-alkoxy-, C$_1$–C$_4$-halogenoalkoxy-, C$_1$–C$_4$-alkylthio-, C$_1$–C$_4$-halogenoalkylthio-, C$_1$–C$_4$-alkylsulphinyl-, C$_1$–C$_4$-alkylsulphonyl- or C$_1$–C$_4$-halogenoalkyl-sulphonylsubstituted heterocyclyl selected from the group consisting of furyl, thienyl, oxazolyl, isoxazolyl, pyrazolyl, pyridyl and pyrimidyl.

2. A phenyluracil according to claim 1, wherein m represents the numbers 0, 1 or 2, n represents the numbers 0, 1 or 2, Q represents O, S, SO, SO$_2$, NH or N(CH$_3$), R$^1$ represents hydrogen, amino or represents in each case optionally cyano-, fluorine-, chlorine-, methoxy- or ethoxy-substituted methyl, ethyl, n- or i-propyl, n-, i-, s- or t-butyl, R$^2$ represents carboxyl, cyano, carbamoyl, thiocarbamoyl, or represents in each case optionally cyano-, fluorine-, chlorine-, methoxy- or ethoxy-substituted methyl, ethyl, n- or i-propyl, n-, i-, s- or t-butyl, methoxycarbonyl, ethoxycarbonyl, n- or i-propoxycarbonyl, R$^3$ represents hydrogen, fluorine, chlorine, bromine, or represents in each case optionally cyano-, fluorine-, chlorine-, methoxy- or ethoxy-substituted methyl, ethyl, n- or i-propyl, n-, i-, s- or t-butyl, R$^4$ represents hydrogen, cyano, fluorine or chlorine, R$^5$ represents nitro, amino, hydroxyl, carboxyl, cyano, carbamoyl, thiocarbamoyl, sulpho, chlorosulphonyl, aminosulphonyl, fluorine, chlorine, bromine, or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, and R$^6$ represents amino or represents one of the groupings below —NH—R$^8$, —N(R$^8$)$_2$, —NH—SO$_2$—R$^8$, —N(R$^8$)(SO$_2$—R$^8$), —N(SO$_2$—R$^8$)$_2$, —NH—CO—R$^9$, —N(R$^8$)(CO—R$^9$), —N(CO—R$^9$)$_2$, —N(SO$_2$—R$^8$)(CO—R$^9$), R$^7$ represents hydroxyl, mercapto, carboxyl, carbamoyl, thiocarbamoyl, sulpho, chlorosulphonyl, aminosulphonyl, fluorine, chlorine, bromine, or represents in each case optionally cyano-, fluorine-, chlorine-, methoxy -or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, acetylamino, propionyl amino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, bis-(methylsulphonyl)-amino or bis-(ethylsulphonyl)-amino, $R^8$ represents in each case optionally fluorine and/or chlorine-substituted methyl, ethyl, n- or i-propyl, n-, i-, s- or t-butyl, represents in each case optionally fluorine- and/or chlorine-substituted ethenyl, propenyl or butenyl, represents in each case optionally cyano-, fluorine-, chlorine-, methyl- or ethyl-substituted cyclopropyl, cyclobutyl, cyclopentyl or cyclohexyl, represents in each case optionally nitro-, cyano-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphonyl-, methylsulphonyl-, ethylsulphonyl-, trifluoromethylsulphonyl-, methoxycarbonyl- or ethoxycarbonyl-substituted phenyl or benzyl, or represents optionally cyano-, fluorine-, chlorine-, bromine-, methyl-, ethyl-, n- or i-propyl-, n-, i-, s- or t-butyl, trifluoromethyl-, methoxy-, ethoxy-, n- or i-propoxy-, n-, i-, s- or t-butoxy-, difluoromethoxy-, trifluoromethoxy-, methylthio-, ethylthio-, n -or i-propylthio-, n-, i-, s- or t-butylthio-, trifluoromethylthio-, methylsulphinyl-, ethylsulphinyl-, trifluoromethylsulphonyl-, methylsulphonyl-, ethylsulphonyl-, or trifluoromethylsulphonyl-substituted heterocyclyl selected from the group consisting of furyl, thienyl, oxazolyl, isoxazolyl, pyrazolyl, pyridyl and pyrimidyl, and $R^9$ represents hydrogen, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino or dimethylamino, represents in each case optionally cyano-, fluorine- or chlorine-substituted ethenyl, propenyl, butenyl, ethenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, thiocarbamoyl-, fluorine-, chlorine-, bromine-, methyl-, ethyl-, n -or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphonyl-, methylsulphonyl-, ethylsulphonyl-, trifluoromethylsulphonyl-, methoxycarbonyl-, ethoxycarbonyl-, n- or i-propoxy-carbonyl-substituted phenyl or benzyl, or represents optionally cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoro-methoxy-, trifluoromethoxy-, methylthio-, ethylthio-, n- or i-propylthio-, trifluoromethylthio-, methylsulphinyl-, ethylsulphinyl-, trifluoromethylsulphinyl-, methylsulphonyl-, ethylsulphonyl- or trifluoromethylsulphonyl- substituted heterocyclyl selected from the group consisting of furyl, thienyl, oxazolyl, isoxazolyl, pyrazolyl, pyridyl and pyrimidyl.

3. A phenyluracil according to claim 1, wherein $R^1$ represents hydrogen.

4. A phenyluracil according to claim 1, wherein $R^6$ represents —NH—$R^8$, —N($R^8$)$_2$, —NH—SO$_2$—$R^8$, —N($R^8$)(SO$_2$—$R^8$), —N(SO$_2$—$R^8$)$_2$, —NH—CO—$R^9$, —N($R^8$)(CO—$R^9$), —N(CO—$R^9$)$_2$, or —N(SO$_2$—$R^8$)(CO—$R^9$).

5. A phenyluracil according to claim 1, wherein $R^1$ represents hydrogen, amino, or cyano-substituted alkyl having 1 to 6 carbon atoms.

6. A phenyluracil according to claim 1, wherein $R^6$ is in the 2, 3 or 5 position of the phenyl ring.

7. A phenyluracil according to claim 1, wherein $R^6$ is in the 3 position of the phenyl ring.

8. A phenyluracil according to claim 1, wherein position 3 of the phenyl ring to which $R^6$ is attached is other than hydrogen.

9. A herbicidal composition comprising one or more phenyluracils according to claim 1 and an extender and/or a surfactant.

10. A method of controlling undesirable plants, comprising applying an effective amount of one or more substituted phenyluracils according to claim 1 to the undesired plant or to the soil or growth medium.

11. A phenyluracil of the formula (I)

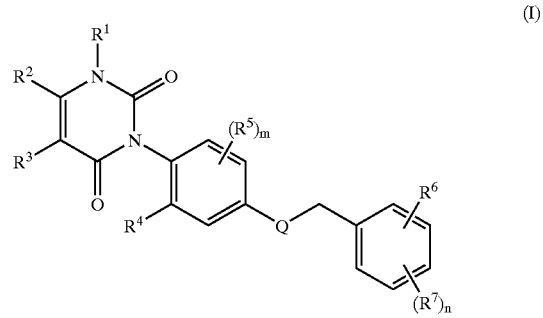

wherein m represents the number 0, n represents the number 1,

Q represents O, $R^1$ represents methyl, $R^2$ represents trifluoromethyl, $R^3$ represents hydrogen, $R^4$ represents fluorine or chlorine, $R^6$ represents, amino, —NH—SO$_2$—$R^8$ or —N(SO$_2$—$R^8$)(CO—$R^9$), $R^7$ represents nitro, cyano, fluorine, chlorine, bromine or represents optionally fluorine-substituted methyl or methoxy, $R^8$ represents methyl or ethyl, and $R^9$ represents methyl, ethyl, n- or i-propyl, n-, i-, s- or t-butyl or phenyl.

* * * * *